(12) United States Patent
Rudde (10) Patent No.: US 9,052,292 B2
(45) Date of Patent: Jun. 9, 2015

(54) METHOD OF DETERMINING A CONCENTRATION OF NITRATE

(75) Inventor: Heinz Rudde, Hueckelhoven (DE)

(73) Assignee: HACH LANGE GMBH, Berlin (DE)

(*) Notice: Subject to any disclaimer, the term of this patent is extended or adjusted under 35 U.S.C. 154(b) by 0 days.

(21) Appl. No.: 14/004,906

(22) PCT Filed: Mar. 7, 2012

(86) PCT No.: PCT/EP2012/053915
§ 371 (c)(1),
(2), (4) Date: Sep. 23, 2013

(87) PCT Pub. No.: WO2012/123308
PCT Pub. Date: Sep. 20, 2012

(65) Prior Publication Data
US 2014/0011283 A1    Jan. 9, 2014

(30) Foreign Application Priority Data

Mar. 15, 2011 (EP) .................................. 11158356

(51) Int. Cl.
*G01N 21/78* (2006.01)
*G01N 21/00* (2006.01)
*G01N 31/22* (2006.01)

(52) U.S. Cl.
CPC ........ *G01N 21/78* (2013.01); *Y10T 436/173076* (2015.01); *Y10T 436/17* (2015.01); *G01N 31/227* (2013.01)

(58) Field of Classification Search
CPC ........ G01N 21/78; G01N 21/00; Y10T 436/17; Y10T 436/173076
USPC .................................................. 436/110, 106
See application file for complete search history.

(56) References Cited

U.S. PATENT DOCUMENTS

| | | |
|---|---|---|
| 4,424,277 A | 1/1984 | Bodart |
| 4,690,902 A | 9/1987 | Bitsch |
| 5,236,848 A | 8/1993 | Bitsch |

OTHER PUBLICATIONS

Hach Company/Hach Lange GmbH, Nitrate, 2007, p. 1-6.*
Grissom, J. T., The Formaldehyde Method for Determining Ammoium Nitrate, The Journal of Industrial Engineering Chemistry, vol. 12, No. 2, Feb. 1920, p. 172-173.*
Y. Kiso et al.: "Visual determination of nitrite and nitrate in waters by color band formation method", Chemosphere, vol. 64, pp. 1949-1954 (2006).

* cited by examiner

*Primary Examiner* — Christine T Mui
(74) *Attorney, Agent, or Firm* — Norman B. Thot (57) ABSTRACT

A method of determining a concentration of nitrate includes mixing an acid with a first mixture comprising an aldehyde, a chloride and at least one of a nitrate sample and distilled water so as to obtain a second mixture. The second mixture is reacted with a phenol so as to develop a color in a third mixture after a reaction time. The concentration of nitrate is determined colorimetrically with the third mixture.

20 Claims, 4 Drawing Sheets

METHOD OF DETERMINING A CONCENTRATION OF NITRATE

CROSS REFERENCE TO PRIOR APPLICATIONS

This application is a U.S. National Phase application under 35 U.S.C. §371 of International Application No. PCT/EP2012/053915, filed on Mar. 7, 2012 and which claims benefit to European Patent Application No. 11158356.3, filed on Mar. 15, 2011. The International Application was published in English on Sep. 20, 2012 as WO 2012/123308 A1 under PCT Article 21(2).

FIELD

The present invention provides a sensitive colorimetric nitrate analysis method. The analysis allows nitrate levels to be determined in a simple manner at µg/l detection levels for a broad spectrum of solutions.

BACKGROUND

The nitrate ion is an oxidative an ion with the Molecular formula $NO_3^-$ and a Molecular mass of 62.0049 g/mol. Nitrate represents the most oxidized chemical form of nitrogen found in natural systems. All living systems require nitrogen to exist since nitrogen is used to build many essential components such as proteins, DNA, RNA and vitamins, as well as hormones and enzymes. Higher organisms such as animals cannot use simple forms of nitrogen, such as nitrate and ammonium, and are instead dependent on complex forms of nitrogen such as amino acids and nucleic acids.

While nitrogen is an essential building block for life, nitrogen in the form of nitrate can also be harmful. When nitrate is taken in by eating food and drinking water, nitrate is converted to nitrite. Nitrite then combines with hemoglobin to form methemoglobin. This process can lead to the Hypoxia (medical) in organ tissue and a dangerous condition called Methemoglobinemia. Methemoglobinemia in infants is known as blue baby syndrome. Infants are more susceptible to nitrate toxicity than older children or adults. While fatalities are rare, sub-acute methemoglobinemia can affect development. Chronic consumption of high levels of nitrate may also cause other health problems, such as cancer or may contribute to disturbing the growth and development of an embryo or fetus. This is because excess nitrite moves into the bloodstream where it binds strongly to blood hemoglobin and impairs the delivery of oxygen to the embryo or fetus. Elevated levels of nitrate also lead to a build-up of nitrite in the gastrointestinal tract by nitrate reducing bacteria. There have recently been reports of a link between nitrate levels in drinking water and bladder cancer in women. Blood and serum nitrate levels can also become elevated as the result of increased production of nitric oxide (NO). Nitric oxide is an unstable gaseous compound that readily diffuses into body fluids where it can be converted to nitrate, nitrite or S-nitrothiol. NO levels rise during heightened immune-response such as occurs during sepsis, organ failure or graft-rejection.

Some adults can be more susceptible to the effects of nitrate than others. The Cytochrome b5 reductase Enzyme may be under-produced or absent in certain people that have an inherited mutation. Such individuals are unable to break down methemoglobin as rapidly as those that have the enzyme, leading to increased circulating levels of methemoglobin with the result that their blood is not as oxygen-rich. Those with insufficient stomach acid may also be at risk. Such individuals may include, for example, vegetarians and vegans. The increased consumption of green, leafy vegetables that typically accompanies vegetarian and vegan diets may lead to increased nitrate intake. While nitrate exposure is most easily caused by drinking water, it can also be caused by eating vegetables with high levels of nitrate. The high levels of nitrate in plants may be caused, for example, by growth conditions such as reduced sunlight, the undersupply of the essential micronutrients molybdenum (Mo) and iron (Fe), or high concentrations of nitrate due to reduced assimilation of nitrate in the plant. High levels of nitrate fertilization also contribute to elevated levels of nitrate in the harvested plant. A wide variety of medical conditions, such as food allergies, asthma, hepatitis, and gallstones may be linked with low stomach acid; these individuals may also be highly sensitive to the effects of nitrate.

Nitrate does not, however, only affect humans. Other animals are also affected. Nitrate can reach such high levels in some Freshwater or Estuary systems close to land so as to potentially cause the death of fish. Nitrate levels over 30 ppm can inhibit growth, impair the immune system and cause stress in some aquatic species. Supplying a nitrogen-limited eco-system with high levels of nitrate can result in significant increases in the levels of phytoplankton (algae) and macrophytes (aquatic plants). This can pose a significant threat to fragile ecosystems. The recommended level of nitrates to avoid the propagation of algal blooms is between 0.1 to 1 mg/L.

Nitrate is a wide spread contaminant of ground and surface waters worldwide. The accumulation of nitrate in the environment is greatly impacted by runoff from the over-application of nitrogen fertilizers. Nitrate contamination can also occur from concentrated animal feeding operations and from poorly or untreated human sewage. Because nitrate is a naturally-occurring chemical that is left after the breakdown or decomposition of animal or human waste, water quality may also be affected if a high number of septic systems exist in a watershed. Septics leach down into groundwater resources or aquifers and supply nearby bodies of water. Lakes that rely on ground water are often affected by nitrification through this process. Nitrate-containing wastes are also produced by many industrial processes including paper and munitions manufacturing. The burning of fossil fuels in power plants and cars, SUVs and all internal combustion engines results in the production of nitric acid and ammonia as air pollution.

Nitrate ion from fertilizers, sewage and manufacturing has reached high concentrations in water supplies throughout the world. The analytical control of nitrate concentrations in surface waters, especially those which serve as drinking water sources, is therefore regulated in most advanced countries. The United States Environmental Protection Agency (EPA) has, for example, established an enforceable regulation for nitrate, called a maximum contaminant level (MCL), at 10 mg/L or 10 ppm. The EPA thereby notes that infants below six months who drink water containing nitrate in excess of the maximum contaminant level could become seriously ill and, if untreated, may die.

Because the major environmental release of nitrate arises from its use in fertilizers, it is unlikely that the nitrate problem will disappear anytime soon. A continued need to monitor nitrates in finished drinking water, watersheds, industrial wastewater, private wells and estuaries exists. Nitrate contamination of source water will also continue to be relevant for industries that depend on water purity for manufacturing their products.

In addition to other well-known specific nitrate determination methods, such as ion chromatography or direct potentiometry (so-called $NO_3$ ISE or ion selective electrode), colorimetric nitrate determination methods currently serve as the "backbone" of nitrate analyses in water laboratories.

One of the current state of the art colorimetric methods is the LCK 339 nitrate kit provided by Hach Lange GmbH. The LCK 339 provides a highly accurate and reliable nitrate analysis for waste water, drinking water, raw water, surface water, soils, substrates and nutrient solutions in the range of 0.23-13.50 mg/L $NO_3$—N with a cuvette path length of 11 mm. The LCK 339 determines the concentration of nitrate based on the principal that nitrate ions in solutions containing high concentrated sulfuric and phosphoric acids react with 2,6-dimethylphenol to form 4-nitro-2,6-dimethylphenol, which can in turn be detected colorimetrically at a wavelength of 340 nm.

The LCK 339 itself improves on known state of the art analytical methods whereby the concentration of $NO_3$—N is colorimetrically determined using 2,6-dimethylphenol. However, said known methods only have a detection range of 0.5-25.0 mg/L $NO_3$—N with a cuvette a path length of 10 mm at a wavelength of 338 nm and are thus inferior to the LCK 339 offered by Hach Lange GmbH.

The colorimetric detection of nitrate levels using the aforementioned methods has several disadvantages. For example, analytical methods using 2,6-dimethylphenol are sensitive to side reactions in the presence of chlorides. This leads to low $NO_3$—N recoveries and places a cap on the detection limit. Samples containing chloride, calcium or nitrite salt can furthermore either not be analyzed or can only be analyzed in a limited fashion. Sea water, brackish water and/or water from municipal wastewater treatment plants having a high salt content therefore usually cannot be analyzed with the aforementioned methods. Nitrate in ultra-pure water and in drinking water having a nitrate concentration below the aforementioned detection limits can also either not be detected or detected only imprecisely using the aforementioned methods. Wavelengths of between about 340 nm and 370 nm are also susceptible to interference which negatively impact detection accuracy.

Other colorimetric nitrate methods such as the Spectroquant® cuvette test 114556 offered by Merck make use of a side reaction, the so-called Liebermann Nitroso Reaction (LNR), in the presence of chlorides to form an intense colored product. This reaction is mainly used for the colorimetric determination of phenols. The application of the LNR as a nitrate analytical method has the disadvantage that long reaction times of at least 30 minutes are necessary for the complete reduction of the nitrate to the nitroso compound if chloride is the sole reducing agent. Measuring earlier would yield imprecise and inaccurate results. Nitrate tests using the LNR generally have a measuring range limit of 0.1 to 3.0 mg $NO_3$—N mg/L using a 16 mm cuvette. The variation coefficient of this method is, however, double that of the variation coefficient of the aforementioned nitrate analysis methods using 2,6-dimethylphenol. The 16 mm thickness of the cuvette is also almost 1.5 times thicker than the 11 mm cuvette used in the 2,6-dimethylphenol analysis method. The preciseness of this analysis method will therefore necessarily be less than that of the 2,6-dimethylphenol analysis method.

Other analytical methods exist to determine nitrate concentrations, however, all have certain disadvantages.

Nitrate concentration can, for example, be indirectly determined by reducing nitrate to nitrite. The reducing agent for this method is usually either granulated and/or activated cadmium or hydrazine salts, both of which are, however, highly poisonous, such that their sale and disposal is prohibited or limited in many countries for environmental reasons. Following reduction, the nitrite ions are then reacted with an aromatic amine to form a diazonium salt in the presence of an acidic buffer. The diazonium salt in turn reacts with N-(1-naphthyl)-ethylene-diamine to form a red-violet azo dye which allows a semi-quantitative visual comparison with a color scale to occur. Test strips, color cubes and color disks based on this principle are available. While easy to use, test strips and color cubes only allow nitrate concentrations to be determined at certain, limited, concentrations, such as, for example, at 0, 1, 2, 5, 10, 20 and 50 ppm $NO_3$—N for the AquaChek® test strips from Hach Lang GmbH. The easy to use color disks allow for a slightly more accurate $NO_3$—N concentration to be determined, but are also limited to an accuracy in the mg/L $NO_3$—N range. The accuracy of the color disk NI-11 from Hach Lange GmbH, for example, is 0-50 mg/L $NO_3$—N. A somewhat more precise evaluation of the absorption of the color test solution is also possible photometrically.

Nitrate concentration can also be accurately measured through complex high-end systems such as the NITRATAX® family of probes or the GANIMEDE laboratory analysers offered by Hach Lange GmbH. The NITRATAX® probes are specifically designed to constantly monitor the concentration of nitrate by direct immersion in activated sludge, wastewater and/or surface water. The NITRATAX® plus sc model, for example, has a very good measuring range of 0.1-100 mg/L $NO_3$—N. The automated GANIMEDE N analyzer offered by Hach Lange GmbH can analyze for total nitrate concentration. The GANIMEDE N operates using reagents to digest unwanted by-products and to thereby provide a "pure" water sample for analysis. Direct UV measurement at approximately 210 nm versus a reference wavelength of approximately 228 nm, high-quality optics and a complex algorithm are used to calculate nitrate concentrations at a very good measuring range of 0.5-150 mg/L $NO_3$—N (after digestion).

SUMMARY

An aspect of the present invention is to provide a colorimetric nitrate analysis method which is easy to use, inexpensive and therefore mass marketable, and which avoids the use of highly toxic reducing agents. A further aspect of the present invention is to provide a colorimetric nitrate analysis method which is significantly more sensitive than comparable mass market colorimetric nitrate analysis methods and which avoids the low $NO_3$—N recoveries in the presence of halogenid salts to date inherent with nitrate analysis methods using 2,6-dimethylphenol.

In an embodiment, the present invention provides a method of determining a concentration of nitrate, which includes mixing an acid with a first mixture of an aldehyde, a chloride and at least one of a nitrate sample and distilled water so as to obtain a second mixture. A phenol is reacted with the second mixture so as to develop a color in a third mixture after a reaction time. The concentration of nitrate is determined colorimetrically with the third mixture.

BRIEF DESCRIPTION OF THE DRAWINGS

The present invention is described in greater detail below on the basis of embodiments and of the drawings in which.

DETAILED DESCRIPTION

In an embodiment of the present invention, the first mixture can, for example, be obtained by mixing a first solution containing the aldehyde with a second solution containing the chloride to obtain an aldehyde-chloride solution, and adding a third solution containing the nitrate sample and/or the distilled water to the aldehyde-chloride solution to obtain a fourth solution as the first mixture. The second mixture can, for example, be obtained by mixing the acid with the fourth solution so as to obtain a fifth solution as the second mixture. The third mixture can, for example, be obtained by reacting a sixth solution containing the phenol with the fifth solution.

With respect to the third solution, the nitrate sample can be mixed with distilled water or it can be used without distilled water. A person of ordinary skill in the art will understand that if only distilled water is used, no nitrate should exist in the sample. The use of distilled water without nitrate in the third solution can therefore be used to obtain a baseline reading of a sample containing no nitrate, for example, for calibration purposes.

In an embodiment of the present invention, the aldehyde is formaldehyde. The formaldehyde can, for example, be provided as a solid, a liquid/solution and/or as a gas. It can also be provided as a compound which will release formaldehyde when reacting with the acid and/or the phenol, such as a formaldehyde-releasing plastic and/or as a formaldehyde-releasing antimicrobial chemical compound. Although the applicants do not wish to be limited to a particular theory, it is believed that the use of formaldehyde as the aldehyde acts as a reaction accelerator and/or a nitrate reducer. The use of formaldehyde in the reaction mixture as an accelerator allows the reaction of the present invention to proceed to completion more quickly than currently-available nitrate analysis systems based on, for example, 2,6-dimethylphenol. The results attained are also more precise and accurate. The method of the present invention has been found to work well, for example, when formaldehyde is provided in an excess ratio to the analyte Nitrate $NO_3$—N, such as in the range of $NO_3$—N:formaldehyde of 1:500 to 1:1.

Examples of compounds which produce formaldehyde when reacting with the acid and the phenol include paraformaldehyde, hexamethylentetramin (Urotropin) and/or sodium formaldehyde sulfoxylate (Rongalit®).

A person of ordinary skill in the art can also provide the formaldehyde using other compounds. It is, for example, also possible to use formaldehyde-releasing plastics. A formaldehyde-releasing plastic is a plastic manufactured with formaldehyde and which subsequently releases formaldehyde through gas emission or through elution processes. Examples of formaldehyde-releasing plastics include formaldehyde resins such as phenol formaldehyde resins, the engineering thermoplastic polyoxymethylene (POM, which is also known as acetal, polyacetal and polyformaldehyde) and melamine resins. These can be used in a variety of forms including, for example, as a plastic granulate and/or as a molded part such as a plastic container. It is therefore possible to incorporate all or part of the formaldehyde in a formaldehyde-releasing plastic container. The chloride and the nitrate sample and/or the distilled water can, for example, be placed in the container so as to react with formaldehyde being released.

It is also possible to provide the formaldehyde through formaldehyde-releasing antimicrobial chemical compounds which are known in the cosmetics industry. Such compounds include, for example, 5-bromo-5-nitro-1,3-dioxane (also known as Bronidox®), 2-bromo-2-nitropropane-1,3-diol (also known as Bronopol), diazolidinyl urea, imidazolidinyl urea, and/or DMDM Hydantoin (also known as 1,3-Bis(hydroxymethyl)-5,5-dimethylimidazolidine-2,4-dione).

It is also possible to use compounds which constitute an intermediate in the ultimate production of formaldehyde. An example for such a compound is methanol which can be oxidized with an alcohol oxidase to formaldehyde.

In an embodiment of the present invention, the chloride can, for example, be an alkali chloride such as lithium chloride, sodium chloride, potassium chloride and/or rubidium chloride. The method has been found to work well, for example, when lithium chloride is used. The amount of chloride used should be in a concentration of, for example, 10 to 100,000 ppm, or, for example, 500 to 50,000 ppm. No chloride need be added separately if, for example, the nitrate sample already contains a sufficient amount of chloride. This might be the case if the nitrate sample is sea water.

In an embodiment of the present invention, the acid has a pH<1, for example, a pH<<1. The acid can, for example, be hydrochloric acid, perchloric acid, sulfuric acid, phosphoric acid, or mixtures thereof. The mixture can be, for example, a mixture of sulfuric acid and phosphoric acid. One possible mixture is, for example, about 60 vol.-% sulfuric acid and 40 vol.-% phosphoric acid.

In an embodiment of the present invention, the phenol is an unsubstituted or substituted mono phenol or diphenol having at least a single aryl group, wherein a nitroso substitution is directed to the para position. Such phenols include, for example, 4-ethyl resorcinol and/or 2,6-dimethylphenol (2,6-xylenol).

Although starting materials in solution or as a liquid can, for example, be used, a person skilled in the art will realize that other starting materials can also be used. The starting materials can, for example, be provided as a solid, freeze-dried, as a powder, immobilized, in tablet form and/or as a combination thereof.

In an embodiment of the present invention, the reaction time should be long enough to allow the color to evolve. A reaction time of up to 20 minutes, for example, from 10 to 15 minutes, has generally been shown to be sufficient. A longer or shorter reaction time may be sufficient based on the starting materials used or external environmental forces such as temperature. Although the applicants do not wish to be limited to a particular theory, it is believed that the color which evolves after the reaction time depends on the type of phenol used. For example, the color is red, reddish and/or pink if the phenol is 2,6-dimethylphenol. The color is blue, bluish and/or violet if the phenol is 4-ethyl resorcinol.

The applicants have not determined the exact nature of the chemistry behind the evolution of the color. The Liebermann Nitroso Reaction (LNR) might, for example, be the basis of the observed color reaction, however, other color producing reactions might also occur.

It is possible that nitrate reacts in the presence of highly concentrated strongly hygroscopic acids with an excess of chlorides to form chlorine ($Cl_2$) and nitrosyl chloride (NOCl) in a nitrate-reducing step. NOCl, as the nitroso compound, would then react with the phenol to form a nitroso phenol as the first reaction of the LNR.

In the LNR, the nitroso phenol reacts with an excess of phenol to form a colored indophenol compound. The color of the compound depends of the pH of the solution and the total water concentration in the reaction mixture. The compound will have a red (I, acidic) and blue (II, alkaline) color, respectively:

In an embodiment of the present invention, the concentration of nitrate can, for example, be colorimetrically determined by measuring an absorption of the third mixture with a photometric device and/or by comparing the color of the third mixture with a pre-determined color spectra such as a color disk and/or color block. Suitable photometric devices are known to those skilled in the art and include, for example, the DR 5000 Spectralphotometer of Hach Lange GmbH. The method of the present invention also allows the absorption to be measured on "low-end" photometric devices such as, for example, the hand held Mini-Colorimeter of Hach Lange GmbH. This is especially practical for field use where only battery power is available.

The red, reddish and/or pink color which evolves if, for example, the phenol 2,6-dimethylphenol is used absorbs at a wavelength of from about 450 nm to about 550 nm, for example, from about 500 nm to about 515 nm. The peak wavelength of absorption is at about 509 nm. The color blue, bluish and/or violet which evolves if, for example, the phenol 4-ethyl resorcinol is used absorbs at a wavelength of from about 540 nm to about 620 nm, for example, from about 565 nm to about 575 nm. The peak wavelength of absorption is at about 570 nm. The photometric device can therefore be respectively preset to the respectively applicable peak wavelength. One advantage of a photometric analysis using the aforementioned wavelengths in comparison to currently-available nitrate analysis methods which use 2,6-dimethylphenol based on the nitrification reaction is that more inexpensive photometric devices can be used. The method of the present invention can therefore be more widely used at lower cost.

The method of the present invention has been shown to have an extrapolated detection limit of 6 µg/L $NO_3$—N in an 11 mm cuvette and a limit of determination of 21 ppb. This detection limit is therefore some 11 times more sensitive than comparable currently-available nitrate analysis methods which use 2,6-dimethylphenol based on the nitrification reaction.

In an embodiment, the present invention also provides a test kit for determining the concentration of nitrate which uses the method as recited above. The test kit as well as the inventive method can be used to determine the concentration of nitrate in, for example, ultrapure water, in drinking water, in municipal wastewater as well as in waters which can contain high amounts of chloride such as sea water and brackish waters. It is also possible to test the nitrate concentration of plants and soils. Plants such as vegetables can, for example, be ground or milled to obtain a liquid extract which can then be tested directly or following a pretreatment, or first diluted with distilled water and then tested with the method of the present invention. Water can also be filtered through soil for subsequent testing. A person of ordinary skill in the art will find the method of the present invention useful in determining the nitrate concentrations of all manner of solutions and objects.

In an embodiment, the present invention can also be combined with existing nitrate analysis methods to perform nitrification. For example, if both test reactions use the same acid mixture and the same phenol compounds such as 2,6-dimethylphenol in the same concentration, the user can decide which of the analysis methods, such as, for example, the nitrification of the state of the art as embodied by the LCK 339 analysis method offered by Hach Lange GmbH, or the analysis method of the present invention, should be used. This use can depend, for example, on the type of sample solution available and/or on the concentration of nitrate expected. If, for example, a sample contains a high concentration of salt, such as sea water or brackish water, or if the expected nitrate concentration is expected to be low, the user can opt to use the analysis method of the present invention. If, on the other hand, a nitrate concentration well in excess of 1 mg/L $NO_3$—N is expected, either the analysis method of the present invention or of the LCK 339, or a similar nitrification analysis method, can be used.

In an embodiment, a combined test kit can, for example, comprise the nitrate analysis method of the present invention and currently available nitrate analysis methods based on 2,6-dimethylphenol. Many of the same compounds are used in both nitrate analysis methods so that a combination of both nitrate analysis methods as a combined/single test kit would provide the greatest possible flexibility for consumers. For example, a consumer may decide to use the analysis method based on 2,6-dimethylphenol (and not chloride and the aldehyde/formaldehyde as per the analysis method of the present invention) to obtain a nitrophenol. Such a method is used, for example, in the LCK 339 currently offered by Hach Lange GmbH. The consumer can additionally and/or alternatively opt to perform the analysis method of the present invention by simply adding chloride and the aldehyde/formaldehyde as described in the present application, and thereby obtain the colored compound and/or compound mix whose color can then be colorimetrically determined.

The present invention will hereafter be described by experiments.

EXPERIMENTAL

General Experimental Procedure

A chloride solution containing 1 ml of 10 M LiCl was prepared as the chloride. To this chloride solution was added 10 µl of a 1% formaldehyde solution as the aldehyde. An aldehyde-chloride solution was thereby obtained containing approximately 10 mol/L LiCl and 2.5 mmol/L formaldehyde.

1 ml of the aldehyde-chloride solution was added to 9 ml of a nitrate sample, which was provided as a solution, as the third solution. 10 ml of a first mixture was thereby obtained. Alternatively, 10 ml of a first mixture can be obtained by adding 1 ml of the aldehyde-chloride solution to 9 ml of distilled water as the third solution if a base detection level for a sample is to be obtained, for example, for calibration purposes. The first mixture in both cases would contain 1 mol/L LiCl and 0.25 mmol/L formaldehyde.

1 ml of the first mixture was then added to an 11 mm cuvette for the optical examination of fluids containing 4 ml of a concentrated acid mixture as the acid. A second mixture was thereby obtained. The specific acid in the cuvette contained 60 vol.-% sulfuric acid and 40 vol.-% of phosphoric acid. The total volume of the second mixture in the cuvette was approximately 5 ml.

A 0.2 ml solution containing an excess (the ratio of 2,6-dimethylphenol:$NO_3$—N can be, for example, 20, 000:1 to 10:1) of 2,6-dimethylphenol as the phenol and 2-propanol as a solubility promoting reagent was pipetted into the second mixture. A third mixture with a volume of 5.2 ml was thereby obtained. This third mixture contained 192 mmol/L LiCl and 48 μmol/L formaldehyde. The cuvette was then sealed and the third mixture was allowed to react for 10 to 15 minutes until a red color developed to stable absorption. The red color of the third mixture was then analyzed with a DR 5000 Spectralphotometer of Hach Lange GmbH to colorimetrically determine the concentration of nitrate as $NO_3$—N.

Example 1

Absorbance Characteristics

Standards containing known amounts of nitrate were tested using the Experimental Procedure set forth above. The standards tested contained 0.0, 0.1, 0.5 and 1.0 ppm concentrations of $NO_3$—N. The chloride content was 50,000 ppm. The absorbance of the standards was then measured colorimetrically with a DR 5000 Spectralphotometer of Hach Lange GmbH at wavelengths of 300 nm to 600 nm.

Figure 1:
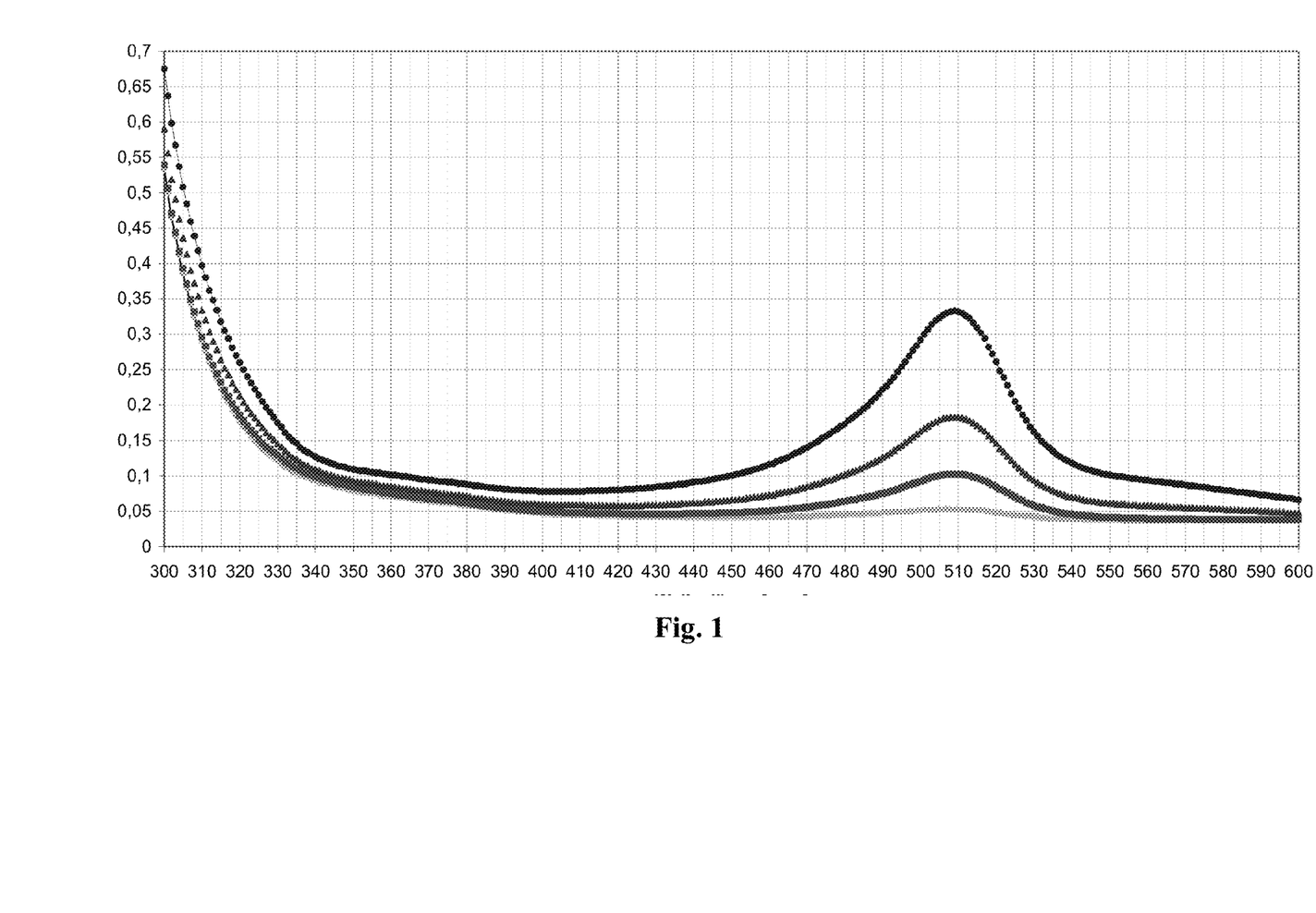
FIG. 1 shows the absorbance of known samples of nitrate in the x axis at corresponding wavelengths in nm set forth in the y axis.

The results are set forth in FIG. 1 which shows the absorbance of the aforementioned nitrate samples in the y axis at corresponding wavelengths in nm in the x axis. A peak dependency can thereby clearly be observed at 509 nm. The peak is also observed to grow when the concentration of nitrate increased. The highest peak therefore existed for a nitrate concentration of 1.0 ppm, followed by 0.5 ppm, 0.1 ppm and 0.0 ppm nitrate concentration, respectively.

Example 2

Sample Calibration

A sample calibration for nitrate concentrations determined pursuant to the method of the present invention was also performed. Standards containing known amounts of nitrate were thereby tested using the Experimental Procedure set forth above. The standards tested contained from 0 to 2,000 ppm of concentrations of $NO_3$—N. The chloride concentration was 35,500 mg/L. The absorbance of the standards was then measured colorimetrically with a DR 5000 Spectralphotometer of Hach Lange GmbH set to a wavelength of 509 nm.

Figure 2:
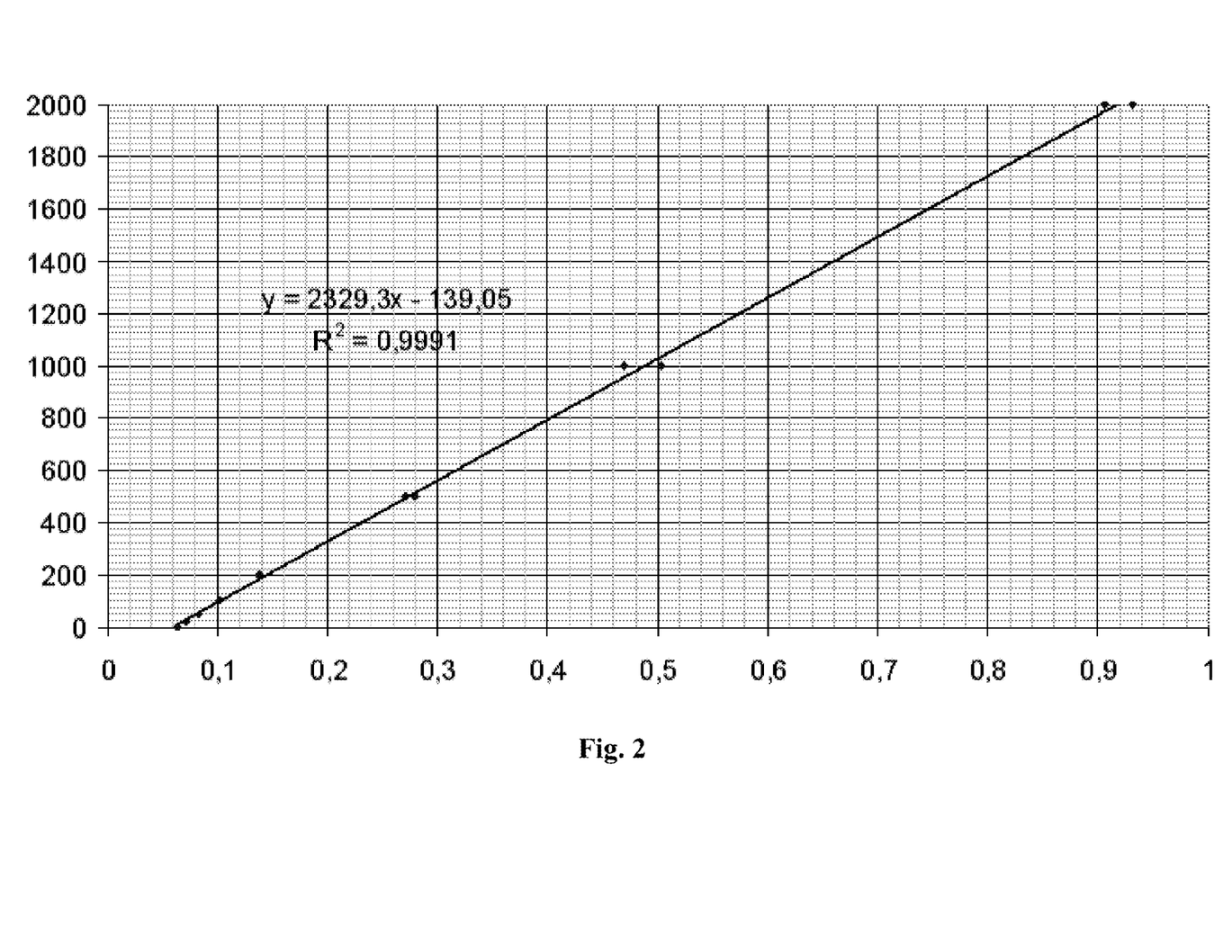
FIG. 2 shows a graphic for a calibration in the range of 0-2,000 ppb nitrate N with the x axis representing the concentration of $NO_3$—N in ppb and the y axis representing absorbance.

The results of the sample calibration are set forth in FIG. 2. FIG. 2 shows a graphic where the y axis represents the concentration of $NO_3$—N in ppb and the x axis represents absorbance. The correlation of $R^2=0.9991$ is excellent. The graphic shows an extrapolated detection level of 20 ppb.

Example 3

Extrapolated Data and Detection Level

A second sample calibration for nitrate concentrations determined pursuant to the method of the present invention was also performed. Standards containing known amounts of nitrate were thereby tested using the Experimental Procedure set forth above. The concentration of the nitrate standards tested and the absorbance peaks colorimetrically measured with a DR 5000 Spectralphotometer of Hach Lange GmbH set to a wavelength of 509 nm are set forth in Table 1.

TABLE 1

| Sample | Nitrate Level in μg/L | Absorption Peak |
|---|---|---|
| 1 | 0.000 | 0.063 |
| 2 | 0.000 | 0.063 |
| 3 | 20.000 | 0.072 |
| 4 | 20.000 | 0.072 |
| 5 | 50.000 | 0.083 |
| 6 | 50.000 | 0.083 |
| 7 | 100.000 | 0.103 |
| 8 | 100.000 | 0.102 |
| 9 | 200.000 | 0.138 |
| 10 | 200.000 | 0.137 |

Figure 3:
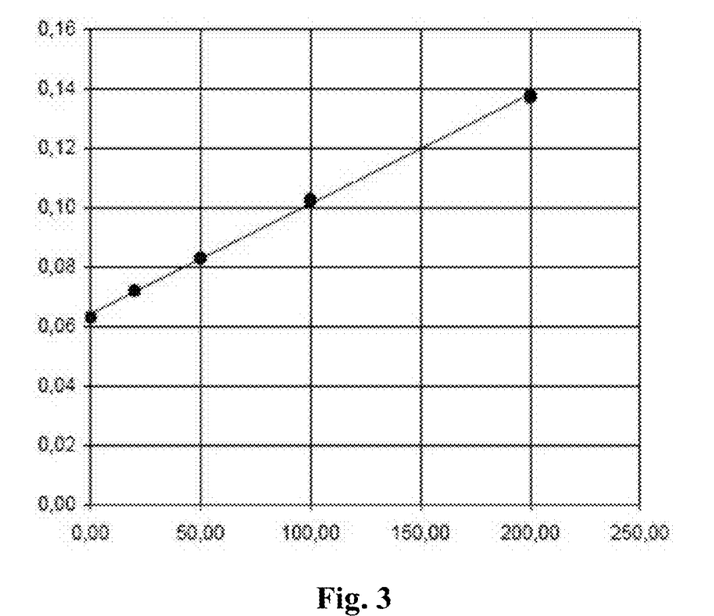
FIG. 3 shows a linear calibration function where the absorbance peak in the y axis is plotted against nitrate concentration set forth in µg/L in the x axis.

The linear calibration of the data in Table 1 is shown in FIG. 3 where the absorption peak in the y axis is plotted against the nitrate concentration in μm/L in the x axis. An excellent correlation coefficient of 0.99938 ($R^2=0.99875$) was thereby obtained at a significance of 95%. The detection limit was 5.766 μg/L. The limit of determination (approximated) was 21.055 μg/L while the limit of determination (exact) was 20.983 μg/L.

Figure 4:
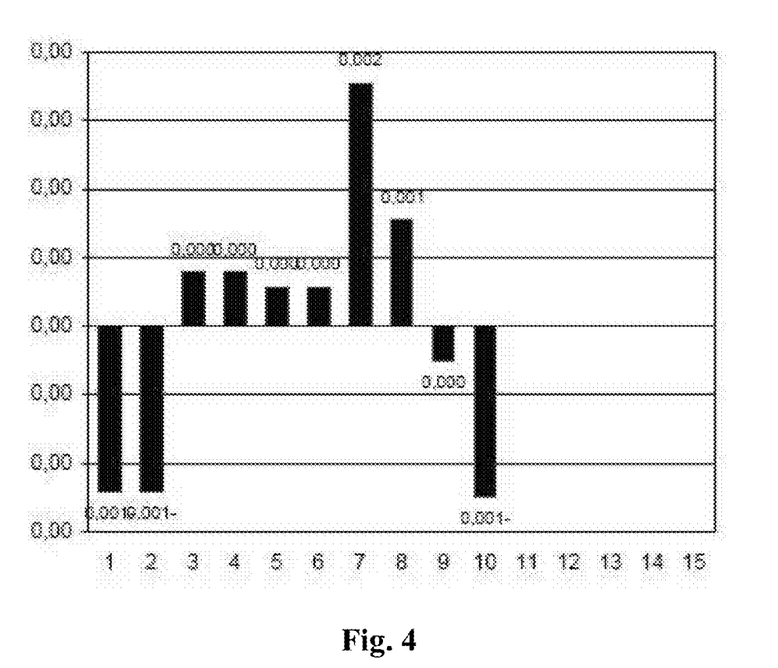
FIG. 4 shows the deviation of the samples from the calculated calibration line in µg/L for 10 nitrate samples.

The deviation of the samples from the calculated calibration line in FIG. 3 in μg/L for the 10 nitrate samples are shown in FIG. 4.

Example 4

Comparison with the State of the Art

The nitrate concentrations of various water samples were determined using the method of the present invention and with the commercially available LCK 339 of Hach Lange GmbH. Four samples were thereby tested as follows:

Sample 1 Drinking water in Benrath, Germany (sample taken Dec. 12, 2010);

Sample 2 Drinking water in Düsseldorf, Germany (sample taken Dec. 29, 2010);

Sample 3 Municipal wastewater from a wastewater plant, Germany (sample taken Aug. 8, 2010); and Sample 4 Municipal wastewater from a wastewater plant, Germany (sample taken Oct. 5, 2010).

Figure 5:
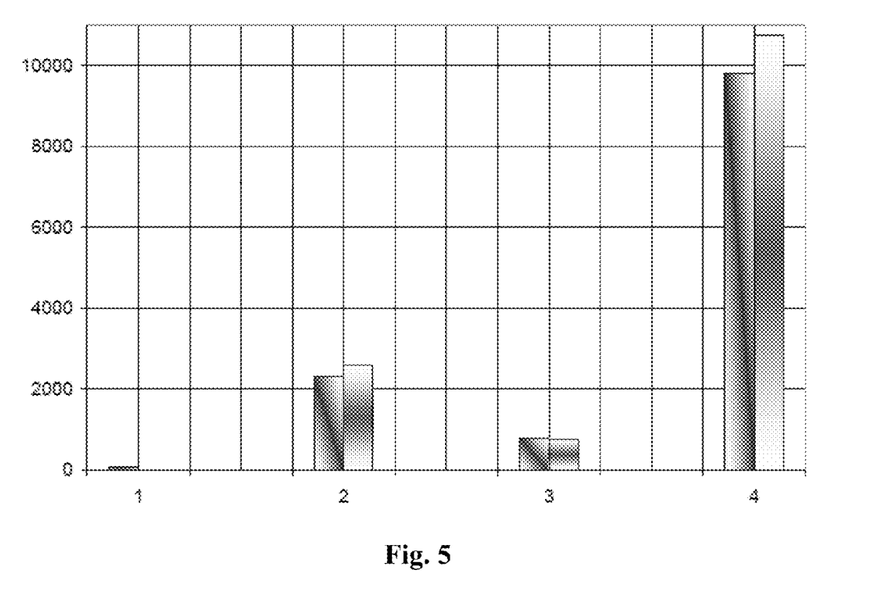
FIG. 5 shows a comparative study of the nitrate analysis method of the present invention compared to the state of the art for various drinking and municipal wastewater sources.

The results of this study are set forth in FIG. 5. The nitrate concentrations determined for each sample tested (1, 2, 3 and 4) are thereby respectively depicted as a pair of bar graphs. The concentration of nitrate determined pursuant to the method of the present invention is thereby always set forth on the left, while the concentration of nitrate determined with the LCK 339 is set forth on the right for each respective pair. The numbers on the left represent the concentration of nitrate as $NO_3$—N in μg/L. The raw data measured is set forth in Table 2.

TABLE 2

| Sample | Inventive Method $NO_3$—N in ppb | LCK 339 $NO_3$—N in ppb |
|---|---|---|
| 1 | 84 | ** |
| 2 | 2,312 | 2,590 |

TABLE 2-continued

| Sample | Inventive Method NO$_3$—N in ppb | LCK 339 NO$_3$—N in ppb |
|---|---|---|
| 3 | 798 | 764 |
| 4 | 9,808 | 10,750 |

** No accurate measurement possible (<<230 ppb LCK 339 detection limit).

FIG. 5 shows that very low nitrate concentrations (<<0.23 mg/L) could not be determined with the LCK 339 while said low nitrate concentrations could be precisely determined using the method of the present invention.

The examples show that the method of the present invention provides a new, highly exact and highly sensitive method of determining nitrate concentrations in a wide variety of solutions. Such solutions include, for example, ultrapure water, drinking water (both having <<230 ppb NO$_3$—N), municipal wastewater and salty water such as sea water and brackish water. The method operates at a wavelength ranging from 460 to 620 nm and can therefore even be used with low end photometers. Any possible UV interference occurring in the area of 300 nm to 370 nm is thereby eliminated. The method can also be used for process applications and for microfluidic systems. It can, for example, easily be used in industry to monitor solutions for nitrate concentrations and can be adapted as a colorimetric test system with use of comparator scales.

Although the present invention has been described and illustrated with reference to specific embodiments thereof, it is not intended that the present invention be limited to those illustrative embodiments. Those skilled in that art will recognize that variations and modifications can be made without departing from the true scope of the present invention as defined by the claims that follow. It is therefore intended to include within the present invention all such variations and modifications as fall within the scope of the appended claims and equivalents thereof.

What is claimed is:

1. A method of determining a concentration of nitrate, the method comprising:
   mixing an acid with a first mixture comprising an aldehyde, a chloride and at least one of a nitrate sample and distilled water so as to obtain a second mixture;
   reacting a phenol with the second mixture so as to develop a color in a third mixture after a reaction time; and
   determining the concentration of nitrate colorimetrically with the third mixture.

2. The method as recited in claim 1, wherein:
   the first mixture is obtained by mixing a first solution containing the aldehyde with a second solution containing the chloride to obtain an aldehyde-chloride solution and adding a third solution containing the at least one of a nitrate sample and distilled water to the aldehyde-chloride solution to obtain a fourth solution as the first mixture,
   the second mixture is obtained by mixing the acid with the fourth solution so as to obtain a fifth solution as the second mixture, and
   the third mixture is obtained by reacting a sixth solution containing the phenol with the fifth solution.

3. The method as recited in claim 1, wherein the aldehyde is formaldehyde.

4. The method as recited in claim 3, wherein the formaldehyde is provided as at least one of a solid, as a liquid/solution, as a gas, as a compound which will produce formaldehyde when reacting with the acid and the phenol, as a formaldehyde-releasing plastic, and as a formaldehyde-releasing antimicrobial chemical compound.

5. The method as recited in claim 4, wherein the compound which will release formaldehyde when reacting with the acid and the phenol includes at least one of paraformaldehyde, hexamethylenetetramine, and sodium formaldehyde sulfoxylate, the formaldehyde-releasing plastic includes at least one of phenol formaldehyde resin, polyoxymethylene, and melamine resin, and the formaldehyde-releasing antimicrobial chemical compound includes at least one of 5-bromo-5-nitro-1,3-dioxane, 2-bromo-2-nitropropane-1,3-diol, diazolidinyl urea, imidazolidinyl urea, and DMDM Hydantoin.

6. The method as recited in claim 1, wherein the chloride is an alkali chloride.

7. The method as recited in claim 6, wherein the alkali chloride is at least one of lithium chloride, sodium chloride, potassium chloride, and rubidium chloride.

8. The method as recited in claim 1, wherein the chloride is used in a concentration of 10 to 100,000 ppm.

9. The method as recited in claim 1, wherein the acid has a pH<1.

10. The method as recited in claim 1, wherein the acid is a mixture of sulfuric acid and phosphoric acid.

11. The method as recited in claim 1, wherein the phenol is an unsubstituted or a substituted monophenol or a diphenol having at least a single aryl group, wherein a nitroso substitution is directed to the a para position.

12. The method as recited in claim 11, wherein the phenol is at least one of 2,6-dimethylphenol (2,6 xylenol) and 4-ethyl resorcinol.

13. The method as recited in claim 1, wherein the reaction time is up to 20 min.

14. The method as recited in claim 1, wherein the color is at least one of red, reddish, pink, blue, bluish, and violet.

15. The method as recited in claim 1, wherein the concentration of nitrate is colorimetrically determined by measuring an absorption of the third mixture with at least one of a photometric device and by comparing the color of the third mixture with a pre-determined color spectra.

16. The method as recited in claim 15, wherein the pre-determined color spectra is at least one of a color disk and a color block.

17. The method as recited in claim 15 wherein the photometric device operates at a wavelength of from about 460 nm to about 540 nm.

18. The method as recited in claim 1, wherein the method has at least one of an extrapolated detection limit of 6 µg/L and a limit of determination of 21 ppb.

19. A test kit for determining the concentration of nitrate, wherein the test kit uses the method as recited in claim 1.

20. The test kit as recited in claim 19, wherein the test kit further uses a second nitrate analysis method based on 2,6-dimethylphenol.

* * * * *